United States Patent [19]

Dietrich

[11] Patent Number: 4,944,039
[45] Date of Patent: Jul. 31, 1990

[54] PROTECTIVE MASK

[76] Inventor: Ursula Dietrich, 1588 Wedgewood, Hillsborough, Calif. 94010

[21] Appl. No.: 357,525

[22] Filed: May 26, 1989

[51] Int. Cl.⁵ .............................................. A61F 9/00
[52] U.S. Cl. .................................................. 2/13; 2/9
[58] Field of Search ............................ 2/9, 10, 11, 13; 351/158

[56] References Cited

U.S. PATENT DOCUMENTS

| | | | |
|---|---|---|---|
| 1,279,884 | 9/1918 | La Roche | 2/206 |
| 1,582,164 | 4/1926 | Burstyn | 2/206 |
| 2,669,717 | 2/1954 | Diggs | 2/427 X |
| 2,774,970 | 12/1956 | Dubois | 2/9 |
| 3,991,753 | 11/1976 | Viesca | 2/9 |
| 4,701,965 | 10/1987 | Landis | 2/9 X |
| 4,821,340 | 4/1989 | Johnson | 351/158 X |
| 4,843,643 | 7/1989 | Parissenti et al. | 2/9 X |

FOREIGN PATENT DOCUMENTS 688227 1/1940 Fed. Rep. of Germany ............. 2/9
513750 10/1939 United Kingdom ....................... 2/9

Primary Examiner—Werner H. Schroeder
Assistant Examiner—Jeanette E. Chapman
Attorney, Agent, or Firm—Ladas & Parry

[57] ABSTRACT

Described herein is a protective face mask attachable to glasses. The mask comprises a thin frame generally formed to cross transversely over the bridge of the nose, below the eyes and across the cheeks of the user; a protective cover attached to the frame and extending freely therefrom to hang in front of the nose and mouth of the user; and attachment hooks for attaching the frame to the glasses.

14 Claims, 1 Drawing Sheet

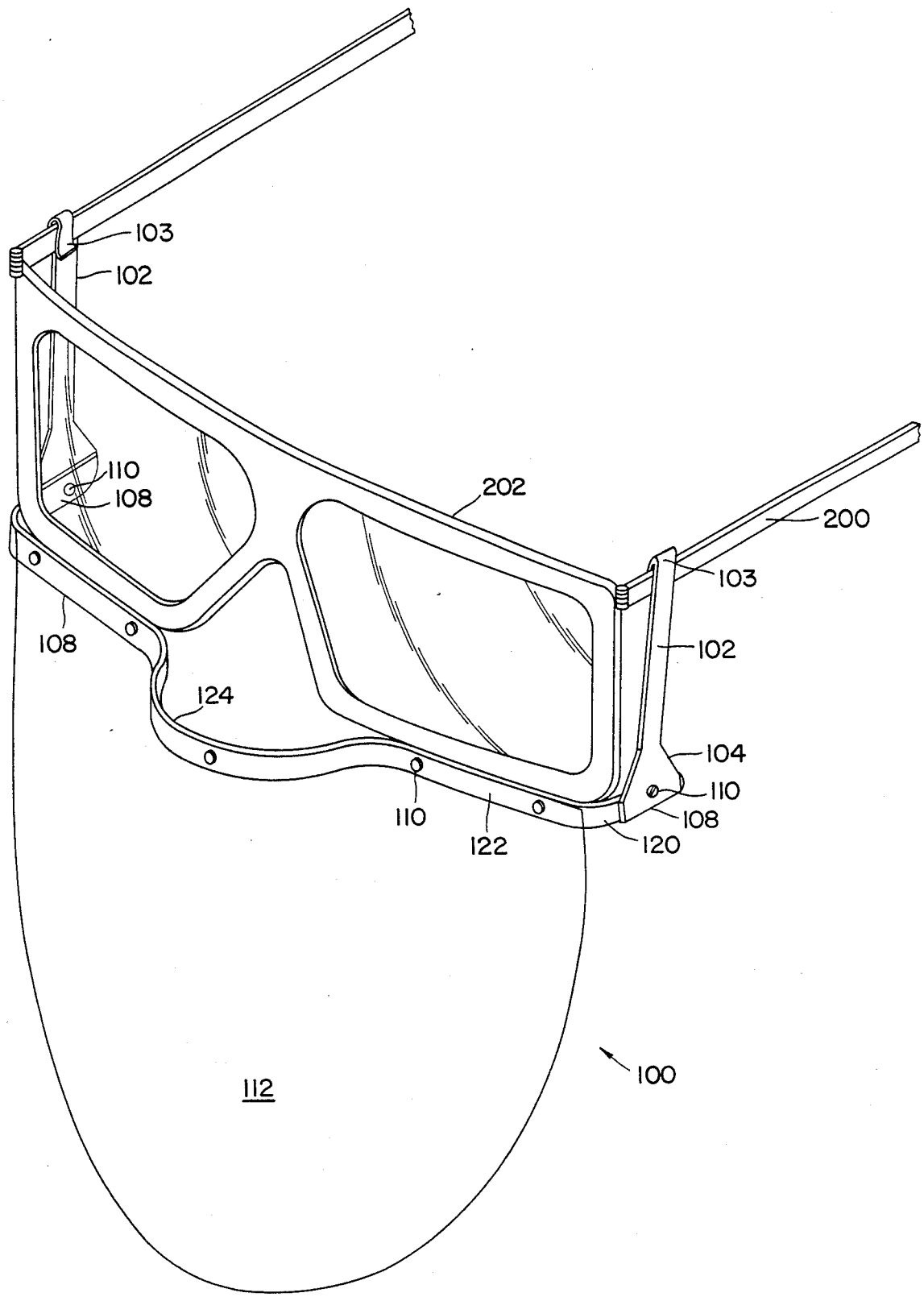

PROTECTIVE MASK

Cross-Applications

A disclosure document bearing number 217554 was filed with the U.S. Patent and Trademark Office by the inventor on Jan. 11, 1988.

BACKGROUND OF THE INVENTION

The present device relates to a means for protecting individuals who must work with the bodily fluids of human beings or animals from direct contact with such fluids. The risk of contacting infectious diseases by contact with bodily fluids of diseased humans and animals has necessitated the use of protective devices so that individuals such as doctors and dentists do not come into direct contact with such fluids. In addition to gowns and gloves, most individuals subject to such exposure wear medical face masks, goggles, and/or glasses. Face masks presently in use tend to restrict breathing to some degree, are uncomfortably warm, muffle to some extent the users speech and are in use somewhat frightening looking to the viewers thereof particularly children. The present invention overcomes these disadvantages.

SUMMARY OF THE INVENTION

Disclosed herein is a protective face mask attachable to glasses, said mask comprising:

a thin frame generally formed to cross transversely over the bridge of the nose, across the cheeks and below the eyes of the user;

a protective mask attached to said frame and extending freely therefrom to hang in front of the nose and mouth of the user; and attachment means for attaching said frame to said glasses.

BRIEF DESCRIPTION OF THE DRAWINGS

The present invention is illustrated in the following drawing.

FIG. 1 is a perspective view of the present invention as attached to a set of glasses.

BRIEF DESCRIPTION OF THE INVENTION

FIG. 1 provides a perspective view of the present invention as applied to a standard pair of glasses. In FIG. 1, the protective mask is generally indicated by numeral (100). It is comprised of two upwardly extending arms (102) located oppositely of one another. Preferably, arms (102) are made of a flexible material such as metal or plastic and are generally rectangular in shape along their body length. At their free ends they define hooks or spring clips (103) which may be connected to glass frames (200). Since the material out of which arms (102) are made is a flexible material, hooks (103) are also flexible and so accommodate various frame shapes. While arms (102) are shown to be preferably rectangular in shape having a greater width than thickness, it is also conceivable that arms (102) could be round, triangular or take on some other geometric shape. At the ends opposite hooks (103), arms (102) widen which widening is identified by numeral (104).

This widening is shown to be of a generally inverted "V" shape. Widening (104) is rotatably pinned or riveted by pins or rivets (110) to shield frame (108). By this rotatable attachment, arms (102) may be angularly adjusted with respect to frame (108). It is within the contemplation of the present invention that arms (102) could be detachably attached to shield frame (108).

Shield frame (108) is to be made of a flexible, plastically deformable material such as metal or plastic and is to be shaped to the general configuration of a face. Thus, shield frame (108) is comprised of: sides (120) which would be located generally parallel to the sides of the user's face; cheek covers (122) which would rest on the cheek bones of the user and are shown flush with the face of glasses (202), and nose protrusion (124). All of these portions (120, 122, 124) are adjustable by bending to ensure user comfort as well as to ensure that the mask (100) rests protectingly on the face of the wearer.

Shield frame (108) is attached to protective cover (112) which is generally "U" shaped and hangs in front of and over the mouth and nose of the user. Preferably, protective cover (112) will extend at least to the chin of the user and preferably slightly below. Protective cover (112) may be made of a clear and generally thin plastic, but could be made of other materials. It is preferably malleable enough or so formed that it adapts to the curvature of shield frame (108) and thereby to the protrusions of the nose and face. In FIG. 1, protective cover (112) is shown riveted by rivets (110) to shield frame (108). The malleability of protective cover (112) is advisable for it to fit comfortably over the nose of the user as well as to bend with any adjustments made to the shield frame (108). While protective cover (112) is shown to extend generally parallel of the front of the face, it may be shaped so that it bends also about the face and even about the sides of the face to extend along the full extension of the shield frame (108). Further, while protective cover (112) is shown pinned or riveted to shield frame (108), it could be affixed in another manner and in fact could be detachably affixed thereto for easy replacement thereof. Thus cover (112) could be disposable. It is suggested that protective cover (112) be clear so that the patient may see the mouth of the user to better assist the patient in understanding comments made by the user and so the general appearance of the user with the mask on is less frightening. It is also suggested that protective cover (112) be impervious to moisture to protect the user from fluids that might splatter onto the mask and otherwise pass through and onto the user.

While the foregoing description has been couched in terms of use of the mask for individuals who are likely to be in contact with bodily fluids, the mask is also useful for other purposes such as by construction workers, painters, artists and beauticians. The mask will aid in preventing inhalation of fumes encountered by such individuals. Such fumes might emanate from paint, paint thinner, permanent formulas and sprays.

It is also to be noted that the mask is fully adjustable to all sorts of glasses and face and nose shapes.

What is claimed:

1. A protective face mask attachable t glasses said mask comprising:

a thin frame generally formed to cross transversely over the bridge of the nose, below the eyes and across the cheeks of the user;

a protective cover attached to said frame and extending freely therefrom to hand in front of the nose and mouth of the user; and attachment means for attaching said frame to said glasses, said attachment means being arms, each arm having a first end and a second end, said first end being rotatably attached to said frame, said second end being attachable by hooking to said glasses.

2. The protective face mask of claim 1 wherein said frame is plastically deformable so that it may be bent to the shape of the user's face.

3. The protective face mask of claim 1 wherein said frame is preformed to the general configuration of a human nose bridge and cheek bones so said frame may rest closely thereto and below the eyes of the user, said frame being plastically deformable for adjustment of said frame shape for different users.

4. The protective face mask of claim 1 wherein said cover is detachably affixed to said frame.

5. The protective face mask of claim 2 wherein said cover is detachably affixed to said frame.

6. The protective face mask of claim 1 wherein said cover is made from a very thin transparent material.

7. The protective face mask of claim 1 wherein said cover is impervious to moisture.

8. The protective face mask of claim 6 wherein said cover is impervious to moisture.

9. The protective face mask of claim 1 wherein said frame extends transversely across the nose of the user and bends about the sides of the face of the user.

10. The protective face mask of claim 1 wherein said protective cover is generally U shaped, the base of said U being in the vicinity of the chin of the user.

11. The protective face mask of claim 1 wherein said mask extends around the sides of the face of the user.

12. The protective face mask of claim 1 wherein said frame is made of metal and wherein said cover is made of plastic.

13. The protective face mask of claim 9 wherein the frame has two ends which lie opposite each other and which rest on the sides of the face of the user, said arms being attached at their first ends to said ends of said frame.

14. A protective face mask attachable to glasses said mask comprising:
a plastically deformable thin frame generally formed to cross transversely over the bridge of the nose, below the eyes and across the cheeks of the user;
a clear plastic protective cover detachably attached to said frame and extending freely therefrom to hang in front of the nose and mouth of the user; and
attachment means for attaching said frame to said glasses, said attachment means being arms, each arm having a first end and a second end, said first end being rotatably attached to said frame, said second end having clips so that said arms may be clipped to said glasses.

* * * * *